United States Patent [19]

Wenderoth et al.

[11] Patent Number: 4,937,372
[45] Date of Patent: Jun. 26, 1990

[54] SUBSTITUTED CROTONATES AND FUNGICIDES CONTAINING THEM

[75] Inventors: Bernd Wenderoth, Lampertheim; Hubert Sauter, Mannheim; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 154,297

[22] Filed: Feb. 10, 1988

[30] Foreign Application Priority Data

Feb. 20, 1987 [DE] Fed. Rep. of Germany ....... 3705389

[51] Int. Cl.$^5$ .............................................. C07C 69/76
[52] U.S. Cl. ...................................... 560/055; 560/21; 560/8; 558/414
[58] Field of Search ............... 560/55, 21, 8; 558/414; 514/532, 535, 543

[56] References Cited

U.S. PATENT DOCUMENTS 4,709,078 11/1987 Schirmer et al. ..................... 560/55

FOREIGN PATENT DOCUMENTS 0178826 3/1985 European Pat. Off. .
988630 2/1962 United Kingdom .

Primary Examiner—Paul J. Killos
Attorney, Agent, or Firm—Oblon, Spivak, McClelland, Maier & Neustadt

[57] ABSTRACT

Substituted crotonates of the formula

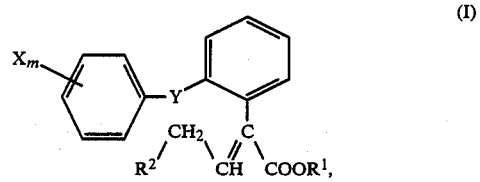

(I)

where $R^1$ is alkyl, $R^2$ is hydrogen, alkyl or alkoxy, X is halogen, cyano, trifluoromethyl, nitro, alkyl, alkoxy, phenyl, phenoxy, benzyloxy or hydrogen, m is from 1 to 5, and Y is methylenoxy, oxymethylene, ethylene, ethenylene, ethynylene or oxygen, and fungicides containing them.

6 Claims, No Drawings

SUBSTITUTED CROTONATES AND FUNGICIDES CONTAINING THEM

The present invention relates to novel crotonate derivatives, their production, and their use as fungicides.

It is known (DE 1 164 162, 1 173 722) to use N-tridecyl-2,6-dimethylmorpholine and its salts, e.g., the acetate, as fungicides. However, their action is in many instances insufficient.

It has also been disclosed (EP 178 826, DE 35 19 282.8, DE 35 19 280.1) that some substituted acrylate derivatives have fungicidal properties.

We have now found that novel crotonate derivatives of the formula I

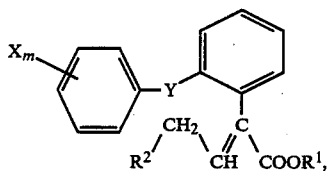

where $R^1$ is $C_1$-$C_5$-alkyl, $R^2$ is hydrogen, $C_1$-$C_4$-alkyl or $C_1$-$C_4$-alkoxy, X is halogen, cyano, trifluoromethyl, nitro, $C_1$-$C_4$-alkyl, $C_1$-$C_4$-alkoxy, substituted or unsubstituted phenyl, substituted or unsubstituted phenoxy, substituted or unsubstituted benzyloxy or hydrogen, the substituents being identical or different when m is greater than 1, m is from 1 to 5, and Y is methylenoxy, oxymethylene, ethylene, ethenylene, ethynylene or oxygen, have an excellent fungitoxic action and are very well tolerated by crop plants.

Because of the C=C double bond, the novel compounds of the formula I are obtained as E/Z isomer mixtures which may be separated into the individual components in conventional manner, e.g., by crystallization or chromatography. The individual isomeric compounds and mixtures thereof are encompassed by the invention.

X is preferably hydrogen, 2-fluoro, 3-fluoro, 4-fluoro, 2-chloro-6-fluoro,2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert.-butyl, 2,4-dimethyl, 2,6-dimethyl, 2,4,6-trimethyl, 2-methoxy-4-methyl, 4-methoxy-2-methyl, 2-methoxy, 3-methoxy, 4-methoxy, 4-ethoxy, 4-isopropoxy, 2-trifluoromethyl, 3-trifluoromethyl, 4-trifluoromethyl, 2-cyano, 3-cyano, 4-cyano, 3-nitro, 4-nitro, 4-phenyl, 4-benzyloxy, 4-phenoxy, halophenoxy, 4-(2-chloro)-phenoxy, 4-(2,4-dichloro)-phenoxy, $C_1$-$C_4$-alkylphenoxy, 4-(2-methyl)-phenoxy, 3-benzyloxy, halobenzyloxy, 3-(2-chloro)-benzyloxy, 3-(2,4-dichloro)-benzyloxy, 3-(2-fluoro)-benzyloxy, 3-(4-bromo)-benzyloxy, $C_1$-$C_4$-alkylbenzyloxy, 3-(2-methyl)-benzyloxy, 3-phenoxy, 3-(2-chloro)-phenoxy, 3-(2,4-dichloro)-phenoxy, 3-(2-fluoro)-phenoxy, 3-(4-bromo)-phenoxy, 3-(2-methyl)-phenoxy, $R^2$ is hydrogen, methyl, ethyl, propyl, butyl, methoxy, ethoxy, isopropoxy, butoxy, $R^1$ is $C_1$-$C_3$-alkyl, methyl, ethyl, isopropyl and Y is a —C$_2$O—, —OCH$_2$—, —CH$_2$—CH$_2$—, CH=CH—, —C≡C— group or is 0.

The novel compounds may be manufactured by reacting an α-ketocarboxylate of the formula II

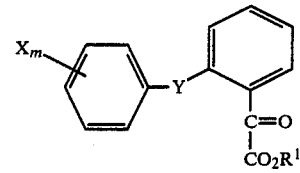

where $X_m$, Y and $R^1$ have the above meanings, in a Wittig reaction with an alkyl- or alkoxymethyltriphenylphosphonium bromide in the presence of a base such as n-butyllithium, sodium methylate, potassium tert-butylate or sodium hydride (cf. G. Wittig and U. Schöllkopf, Coll. Vol. V, 751–4, 1973).

The α-ketocarboxylates of the formula II may be manufactured for example by reacting the corresponding aromatic Grignard compounds with imidazolides of the formula III

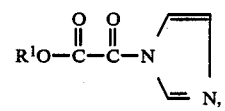

where $R^1$ has the above meanings (J. S. Nimitz, H. S. Mosher, J. Org. Chem., 1981, 46, 211–213).

The manufacture of the novel compounds of the formula I is illustrated by the following example.

MANUFACTURING EXAMPLE (a) Methyl 2-(benzoyloxy)-phenylglyoxylate 0.1 mole of the Grignard compound prepared from 1-benzyloxy-2-bromobenzene and magnesium shavings in tetrahydrofuran is slowly dripped, under nitrogen and at −50° C., to 14.6 g (95 mmol) of methyloxalyl imidazole in tetrahydrofuran. The mixture is slowly allowed to rise to room temperature (20° C.) over a period of 4 hours. The mixture is then poured into ice water and extracted several times with ether. The combined ether phases are washed with water until neutral, and dried. After the solvent has been evaporated off, the product is crystallized with n-pentane. 16 g (62%) of colorless crystals of the abovementioned compound are obtained.

$^1$H-NMR (CDCl$_3$): δ=3.35 (S, 3H), 5.07 (S, 2H), 7.05 (m, 2H) 7.40 (m, 5H), 7.55 (m, 1H), 7.90 (m, 1H).

(b) Methyl 2-[2-(benzyloxy)-phenyl]-crotonate (compound no. 83)

At 0° C. and under nitrogen, 32 ml (50 mmol) of a 1.6 molar solution of n-butyllithium in hexane is slowly added to 18.5 g (50 mmol) of ethyltriphenylphosphonium bromide in 100 ml of absolute tetrahydrofuran. After the mixture has been stirred for 30 minutes, 13.5 g (50 mmol) of methyl 2-(benzyloxy)-phenylglyoxylate in 25 ml of absolute tetrahydrofuran is dripped in at 0° C. The mixture is stirred for 16 hours at room temperature. After concentration, the residue is taken up in dichloromethane and washed several times with water. After drying over Na$_2$SO$_4$ the solvent is evaporated off. The crude product obtained is purified by chromatography (a 9:1 mixture of cyclohexane and ethyl acetate). There is obtained 8.0 g (57%) of the methyl crotonate (trans:-cis ratio=9:1) as an oil.

$^1$H-NMR (CDCl$_3$): δ=1.75/2.12 (2xd, 3H), 3.57/3.64 (2xs, 3H), 5.10 (S, 2H), 6.30/6.90 (2xq, 1H), 6.95–7.80 (m, 9H).

By appropriate modification of the above details, the compounds given in the following tables may be synthesized.

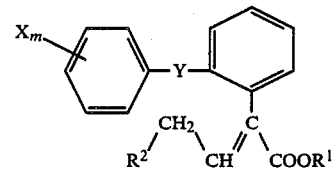

(I)

| Comp. No. | $X_m$ | Y | R$^1$ | R$^2$ | IR(cm$^{-1}$) |
|---|---|---|---|---|---|
| 1 | H | —CH$_2$—CH$_2$— | CH$_3$ | H | |
| 2 | 2-F | —CH$_2$—CH$_2$— | CH$_3$ | H | |
| 3 | 3-F | —CH$_2$—CH$_2$— | CH$_3$ | H | |
| 4 | 4-F | —CH$_2$—CH$_2$— | CH$_3$ | H | |
| 5 | 2-Cl, 6-F | —CH$_2$—CH$_2$— | CH$_3$ | H | |
| 6 | 2-Cl | —CH$_2$—CH$_2$— | CH$_3$ | H | |
| 7 | 3-Cl | —CH$_2$—CH$_2$— | CH$_3$ | H | |
| 8 | 4-Cl | —CH$_2$—CH$_2$— | CH$_3$ | H | |
| 9 | 2-Br | —CH$_2$—CH$_2$— | CH$_3$ | H | |
| 10 | 3-Br | —CH$_2$—CH$_2$— | CH$_3$ | H | |
| 11 | 4-Br | —CH$_2$—CH$_2$— | CH$_3$ | H | |
| 12 | 2,4-Cl$_2$ | —CH$_2$—CH$_2$— | CH$_3$ | H | |
| 13 | 2,6-Cl$_2$ | —CH$_2$—CH$_2$— | CH$_3$ | H | |
| 14 | 3,5-Cl$_2$ | —CH$_2$—CH$_2$— | CH$_3$ | H | |
| 15 | 2,4,6-Cl$_3$ | —CH$_2$—CH$_2$— | CH$_3$ | H | |
| 16 | 2-Cl, 4-CH$_3$ | —CH$_2$—CH$_2$— | CH$_3$ | H | |
| 17 | 2-CH$_3$, 4-Cl | —CH$_2$—CH$_2$— | CH$_3$ | H | |
| 18 | 2-CH$_3$ | —CH$_2$—CH$_2$— | CH$_3$ | H | |
| 19 | 3-CH$_3$ | —CH$_2$—CH$_2$— | CH$_3$ | H | |
| 20 | 4-CH$_3$ | —CH$_2$—CH$_2$— | CH$_3$ | H | |
| 21 | 4-C$_2$H$_5$ | —CH$_2$—CH$_2$— | CH$_3$ | H | |
| 22 | 4-i-C$_3$H$_7$ | —CH$_2$—CH$_2$— | CH$_3$ | H | |
| 23 | 4-t-C$_4$H$_9$ | —CH$_2$—CH$_2$— | CH$_3$ | H | |
| 24 | 2,4-(CH$_3$)$_2$ | —CH$_2$—CH$_2$— | CH$_3$ | H | |
| 25 | 2,6-(CH$_3$)$_2$ | —CH$_2$—CH$_2$— | CH$_3$ | H | |
| 26 | 2,4,6-(CH$_3$)$_3$ | —CH$_2$—CH$_2$— | CH$_3$ | H | |
| 27 | 2-OCH$_3$, 4-CH$_3$ | —CH$_2$—CH$_2$— | CH$_3$ | H | |
| 28 | 4-OCH$_3$, 2-CH$_3$ | —CH$_2$—CH$_2$— | CH$_3$ | H | |
| 29 | 2-OCH$_3$ | —CH$_2$—CH$_2$— | CH$_3$ | H | |
| 30 | 3-OCH$_3$ | —CH$_2$—CH$_2$— | CH$_3$ | H | |
| 31 | 4-OCH$_3$ | —CH$_2$—CH$_2$— | CH$_3$ | H | |
| 32 | 4-OC$_2$H$_5$ | —CH$_2$—CH$_2$— | CH$_3$ | H | |
| 33 | 4-O-i-C$_3$H$_7$ | —CH$_2$—CH$_2$— | CH$_3$ | H | |
| 34 | 2-CF$_3$ | —CH$_2$—CH$_2$— | CH$_3$ | H | |
| 35 | 3-CF$_3$ | —CH$_2$—CH$_2$— | CH$_3$ | H | |
| 36 | 4-CF$_3$ | —CH$_2$—CH$_2$— | CH$_3$ | H | |
| 37 | 2-CN | —CH$_2$—CH$_2$— | CH$_3$ | H | |
| 38 | 4-CN | —CH$_2$—CH$_2$— | CH$_3$ | H | |
| 39 | 3-NO$_2$ | —CH$_2$—CH$_2$— | CH$_3$ | H | |
| 40 | 4-NO$_2$ | —CH$_2$—CH$_2$— | CH$_3$ | H | |
| 41 | 4-C$_6$H$_5$ | —CH$_2$—CH$_2$— | CH$_3$ | H | |
| 42 | H | —CH=CH— | CH$_3$ | H | |
| 43 | 2-F | —CH=CH— | CH$_3$ | H | |
| 44 | 3-F | —CH=CH— | CH$_3$ | H | |
| 45 | 4-F | —CH=CH— | CH$_3$ | H | |
| 46 | 2-Cl, 6-F | —CH=CH— | CH$_3$ | H | |
| 47 | 2-Cl | —CH=CH— | CH$_3$ | H | |
| 48 | 3-Cl | —CH=CH— | CH$_3$ | H | |
| 49 | 4-Cl | —CH=CH— | CH$_3$ | H | |
| 50 | 2-Br | —CH=CH— | CH$_3$ | H | |
| 51 | 3-Br | —CH=CH— | CH$_3$ | H | |
| 52 | 4-Br | —CH=CH— | CH$_3$ | H | |
| 53 | 2,4-Cl$_2$ | —CH=CH— | CH$_3$ | H | |
| 54 | 2,6-Cl$_2$ | —CH=CH— | CH$_3$ | H | |
| 55 | 3,5-Cl$_2$ | —CH=CH— | CH$_3$ | H | |
| 56 | 2,4,6-Cl$_3$ | —CH=CH— | CH$_3$ | H | |
| 57 | 2-Cl, 4-CH$_3$ | —CH=CH— | CH$_3$ | H | |
| 58 | 2-CH$_3$, 4-Cl | —CH=CH— | CH$_3$ | H | |
| 59 | 2-CH$_3$ | —CH=CH— | CH$_3$ | H | |
| 60 | 3-CH$_3$ | —CH=CH— | CH$_3$ | H | |
| 61 | 4-CH$_3$ | —CH=CH— | CH$_3$ | H | |
| 62 | 4-C$_2$H$_5$ | —CH=CH— | CH$_3$ | H | |
| 63 | 4-i-C$_3$H$_7$ | —CH=CH— | CH$_3$ | H | |
| 64 | 4-t-C$_4$H$_9$ | —CH=CH— | CH$_3$ | H | |
| 65 | 2,4-(CH$_3$)$_2$ | —CH=CH— | CH$_3$ | H | |
| 66 | 2,6-(CH$_3$)$_2$ | —CH=CH— | CH$_3$ | H | |
| 67 | 2,4,6-(CH$_3$)$_3$ | —CH=CH— | CH$_3$ | H | |

-continued

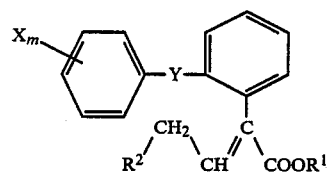

(I)

| Comp. No. | $X_m$ | Y | $R^1$ | $R^2$ | IR(cm$^{-1}$) |
|---|---|---|---|---|---|
| 68 | 2-OCH$_3$, 4-CH$_3$ | —CH=CH— | CH$_3$ | H | |
| 69 | 4-OCH$_3$, 2-CH$_3$ | —CH=CH— | CH$_3$ | H | |
| 70 | 2-OCH$_3$ | —CH=CH— | CH$_3$ | H | |
| 71 | 3-OCH$_3$ | —CH=CH— | CH$_3$ | H | |
| 72 | 4-OCH$_3$ | —CH=CH— | CH$_3$ | H | |
| 73 | 4-OC$_2$H$_5$ | —CH=CH— | CH$_3$ | H | |
| 74 | 4-O-iC$_3$H$_7$ | —CH=CH— | CH$_3$ | H | |
| 75 | 2-CF$_3$ | —CH=CH— | CH$_3$ | H | |
| 76 | 3-CF$_3$ | —CH=CH— | CH$_3$ | H | |
| 77 | 4-CF$_3$ | —CH=CH— | CH$_3$ | H | |
| 78 | 2-CN | —CH=CH— | CH$_3$ | H | |
| 79 | 4-CN | —CH=CH— | CH$_3$ | H | |
| 80 | 3-NO$_2$ | —CH=CH— | CH$_3$ | H | |
| 81 | 4-NO$_2$ | —CH=CH— | CH$_3$ | H | |
| 82 | 4-C$_6$H$_5$ | —CH=CH— | CH$_3$ | H | |
| 83 | H | —CH$_2$O— | CH$_3$ | H | 2950, 1717, 1490, 1419, 1259, 1038, 754, 697 |
| 84 | 2-F | —CH$_2$O— | CH$_3$ | H | 2955, 1718, 1495, 1451, 1259, 1234, 1039, 757 |
| 85 | 3-F | —CH$_2$O— | CH$_3$ | H | 2950, 1716, 1488, 1439, 1256, 1039, 753 |
| 86 | 4-F | —CH$_2$O— | CH$_3$ | H | 2950, 1716, 1512, 1260, 1226, 1038, 754 |
| 87 | 2-Cl, 6-F | —CH$_2$O— | CH$_3$ | H | |
| 88 | 2-Cl | —CH$_2$O— | CH$_3$ | H | 2950, 1718, 1492, 1450, 1259, 1033, 752 |
| 89 | 3-Cl | —CH$_2$O— | CH$_3$ | H | 2950, 1716, 1492, 1450, 1259, 1039, 754 |
| 90 | 4-Cl | —CH$_2$O— | CH$_3$ | H | 2950, 1714, 1494, 1438, 1260, 1040, 754 |
| 91 | 2-Br | —CH$_2$O— | CH$_3$ | H | |
| 92 | 3-Br | —CH$_2$O— | CH$_3$ | H | |
| 93 | 4-Br | —CH$_2$O— | CH$_3$ | H | |
| 94 | 2,4-Cl$_2$ | —CH$_2$O— | CH$_3$ | H | |
| 95 | 2,6-Cl$_2$ | —CH$_2$O— | CH$_3$ | H | |
| 96 | 3,5-Cl$_2$ | —CH$_2$O— | CH$_3$ | H | |
| 97 | 2,4,6-Cl$_3$ | —CH$_2$O— | CH$_3$ | H | |
| 98 | 2-CH$_3$, 4-Cl | —CH$_2$O— | CH$_3$ | H | |
| 99 | 2-Cl, 4-CH$_3$ | —CH$_2$O— | CH$_3$ | H | |
| 100 | 2-CH$_3$ | —CH$_2$O— | CH$_3$ | H | 2960, 1712, 1491, 1448, 1264, 1240, 1034, 762 |
| 101 | 3-CH$_3$ | —CH$_2$O— | CH$_3$ | H | 2960, 1718, 1494, 1450, 1258, 1239, 1040, 753 |
| 102 | 4-CH$_3$ | —CH$_2$O— | CH$_3$ | H | 2950, 1718, 1491, 1451, 1260, 1238, 1039, 753 |
| 103 | 4-C$_2$H$_5$ | —CH$_2$O— | CH$_3$ | H | |
| 104 | 4-i-C$_3$H$_7$ | —CH$_2$O— | CH$_3$ | H | |
| 105 | 4-t-C$_4$H$_9$ | —CH$_2$O— | CH$_3$ | H | |
| 106 | 2,4-(CH$_3$)$_2$ | —CH$_2$O— | CH$_3$ | H | |
| 107 | 2,6-(CH$_3$)$_2$ | —CH$_2$O— | CH$_3$ | H | |
| 108 | 2,4,6-(CH$_3$)$_3$ | —CH$_2$O— | CH$_3$ | H | |
| 109 | 2-OCH$_3$, 4-CH$_3$ | —CH$_2$O— | CH$_3$ | H | |
| 110 | 4-OCH$_3$, 2-CH$_3$ | —CH$_2$O— | CH$_3$ | H | |
| 111 | 2-OCH$_3$ | —CH$_2$O— | CH$_3$ | H | |
| 112 | 3-OCH$_3$ | —CH$_2$O— | CH$_3$ | H | 2950, 1717, 1599, 1493, 1267, 1040, 755 |
| 113 | 4-OCH$_3$ | —CH$_2$O— | CH$_3$ | H | |
| 114 | 4-OC$_2$H$_5$ | —CH$_2$O— | CH$_3$ | H | |
| 115 | 4-O-i-C$_3$H$_7$ | —CH$_2$O— | CH$_3$ | H | |
| 116 | 2-CF$_3$ | —CH$_2$O— | CH$_3$ | H | |
| 117 | 3-CF$_3$ | —CH$_2$O— | CH$_3$ | H | 2945, 1716, 1493, 1448, 1332, 1260, 1166, 1124 |
| 118 | 4-CF$_3$ | —CH$_2$O— | CH$_3$ | H | |
| 119 | 2-CN | —CH$_2$O— | CH$_3$ | H | |
| 120 | 4-CN | —CH$_2$O— | CH$_3$ | H | |
| 121 | 3-NO$_2$ | —CH$_2$O— | CH$_3$ | H | |
| 122 | 4-NO$_2$ | —CH$_2$O— | CH$_3$ | H | |
| 123 | 4-C$_6$H$_5$ | —CH$_2$O— | CH$_3$ | H | |
| 124 | H | —OCH$_2$— | CH$_3$ | H | 2950, 1716, 1598, 1496, 1245, 1036, 754 |

-continued

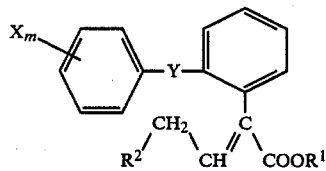

(I)

| Comp. No. | $X_m$ | Y | $R^1$ | $R^2$ | IR(cm$^{-1}$) |
|---|---|---|---|---|---|
| 125 | 2-F | —OCH$_2$— | CH$_3$ | H | 2950, 1714, 1505, 1258, 1038, 748 |
| 126 | 2-Cl | —OCH$_2$— | CH$_3$ | H | 2950, 1715, 1484, 1250, 1061, 1041, 749 |
| 127 | 4-Cl | —OCH$_2$— | CH$_3$ | H | |
| 128 | 2,4-Cl$_2$ | —OCH$_2$— | CH$_3$ | H | |
| 129 | 2-CH$_3$, 4-Cl | —OCH$_2$— | CH$_3$ | H | |
| 130 | 2-CH$_3$ | —OCH$_2$— | CH$_3$ | H | |
| 131 | 4-CH$_3$ | —OCH$_2$— | CH$_3$ | H | 2950, 1717, 1510, 1248, 1038, 818, 764 |
| 132 | 4-t-C$_4$H$_9$ | —OCH$_2$— | CH$_3$ | H | |
| 133 | 2-OCH$_3$ | —OCH$_2$— | CH$_3$ | H | |
| 134 | 2-CF$_3$ | —OCH$_2$— | CH$_3$ | H | |
| 135 | 4-NO$_2$ | —OCH$_2$— | CH$_3$ | H | |
| 136 | H | ethynylene | CH$_3$ | H | |
| 137 | 2-F | ethynylene | CH$_3$ | H | |
| 138 | 2-Cl | ethynylene | CH$_3$ | H | |
| 139 | 2-Br | ethynylene | CH$_3$ | H | |
| 140 | 4-Br | ethynylene | CH$_3$ | H | |
| 141 | 2-CH$_3$ | ethynylene | CH$_3$ | H | |
| 142 | 4-CH$_3$ | ethynylene | CH$_3$ | H | |
| 143 | 2-OCH$_3$ | ethynylene | CH$_3$ | H | |
| 144 | 4-CF$_3$ | ethynylene | CH$_3$ | H | |
| 145 | 2-NO$_2$ | ethynylene | CH$_3$ | H | |
| 146 | H | —CH$_2$O— | CH$_3$ | CH$_3$ | 2970, 1718, 1490, 1449, 1266, 1245, 1042, 753 |
| 147 | H | —CH$_2$O— | CH$_3$ | C$_2$H$_5$ | |
| 148 | H | —CH$_2$O— | CH$_3$ | C$_3$H$_7$ | |
| 149 | H | —CH$_2$O— | CH$_3$ | C$_4$H$_9$ | |
| 150 | H | —CH$_2$O— | CH$_3$ | OCH$_3$ | |
| 151 | H | —CH$_2$O— | CH$_3$ | OC$_2$H$_5$ | |
| 152 | H | —CH$_2$O— | CH$_3$ | O-i-C$_3$H$_7$ | |
| 153 | H | —CH$_2$O— | CH$_3$ | OC$_4$H$_9$ | |
| 154 | H | —CH=CH— | C$_2$H$_5$ | CH$_3$ | |
| 155 | H | —CH$_2$—CH$_2$— | C$_2$H$_5$ | CH$_3$ | |
| 156 | H | —CH=CH— | i-C$_3$H$_7$ | CH$_3$ | |
| 157 | H | —CH$_2$—CH$_2$— | i-C$_3$H$_7$ | CH$_3$ | |
| 158 | H | —CH=CH— | CH$_3$ | CH$_3$ | |
| 159 | H | —CH$_2$—CH$_2$— | CH$_3$ | CH$_3$ | |
| 160 | H | O | CH$_3$ | H | |
| 161 | 2-F | O | CH$_3$ | H | |
| 162 | 2-Cl | O | CH$_3$ | H | |
| 163 | 2-Br | O | CH$_3$ | H | |
| 164 | 4-Br | O | CH$_3$ | H | |
| 165 | 4-Cl | O | CH$_3$ | H | |
| 166 | 2-CH$_3$ | O | CH$_3$ | H | |
| 167 | 4-CH$_3$ | O | CH$_3$ | H | |
| 168 | 2-OCH$_3$ | O | CH$_3$ | H | |
| 169 | 4-OCH$_3$ | O | CH$_3$ | H | |
| 170 | 4-C$_6$H$_5$ | O | CH$_3$ | H | |
| 171 | H | —CH=CH— | CH$_3$ | OCH$_3$ | |
| 172 | H | —CH$_2$—CH$_2$— | CH$_3$ | OCH$_3$ | |
| 173 | 4-OCH$_2$—C$_6$H$_5$ | —CH=CH$_2$— | CH$_3$ | H | |
| 174 | 4-OCH$_2$—C$_6$H$_5$ | —CH$_2$—CH$_2$— | CH$_3$ | H | |
| 175 | 4-OC$_6$H$_5$ | —CH=CH— | CH$_3$ | H | |
| 176 | 4-OC$_6$H$_5$ | —CH$_2$—CH$_2$— | CH$_3$ | H | |
| 177 | 4-O—C$_6$H$_4$(3-Cl) | —CH$_2$—CH$_2$— | CH$_3$ | H | |
| 178 | 4-O—C$_6$H$_3$(2-Cl, 4-Cl) | —CH$_2$—CH$_2$— | CH$_3$ | H | |

-continued
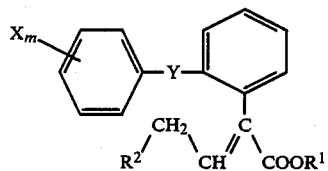
(I)
| Comp. No. | $X_m$ | Y | $R^1$ | $R^2$ | IR(cm$^{-1}$) |
|---|---|---|---|---|---|
| 179 | 4-O-(2-CH$_3$-phenyl) | —CH$_2$—CH$_2$— | CH$_3$ | H | |
| 180 | 3-OCH$_2$—C$_6$H$_5$ | —CH$_2$—CH$_2$— | CH$_3$ | H | |
| 181 | 3-OCH$_2$-(2-Cl-phenyl) | —CH$_2$—CH$_2$— | CH$_3$ | H | |
| 182 | 3-OCH$_2$-(2,4-diCl-phenyl) | —CH$_2$—CH$_2$— | CH$_3$ | H | |
| 183 | 3-OCH$_2$-(2-F-phenyl) | —CH$_2$—CH$_2$— | CH$_3$ | H | |
| 184 | 3-OCH$_2$-(4-Br-phenyl) | —CH$_2$—CH$_2$— | CH$_3$ | H | |
| 185 | 3-OCH$_2$-(2-CH$_3$-phenyl) | —CH$_2$—CH$_2$— | CH$_3$ | H | |
| 186 | 3-OC$_6$H$_5$ | —CH$_2$—CH$_2$— | CH$_3$ | H | |
| 187 | 3-O-(2-Cl-phenyl) | —CH$_2$—CH$_2$— | CH$_3$ | H | |
| 188 | 3-O-(2,4-diCl-phenyl) | —CH$_2$—CH$_2$— | CH$_3$ | H | |

-continued

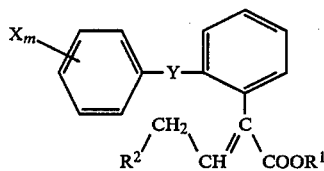

| Comp. No. | $X_m$ | Y | $R^1$ | $R^2$ | IR(cm$^{-1}$) |
|---|---|---|---|---|---|
| 189 | 3-O—⌬—F | —CH$_2$—CH$_2$— | CH$_3$ | H | |
| 190 | 3-O—⌬—Br | —CH$_2$—CH$_2$— | CH$_3$ | H | |
| 191 | 3-O—⌬—CH$_3$ | —CH$_2$—CH$_2$— | CH$_3$ | H | |
| 192 | 3-OCH$_3$ | —CH$_2$—O— | CH$_3$ | CH$_3$ | 2960, 1716, 1599, 1492, 1267, 1246, 1042, 754 |
| 193 | H | —OCH$_2$— | CH$_3$ | CH$_3$ | 2960, 1717, 1599, 1496, 1242, 1040, 753 |
| 194 | 2-F | —OCH$_2$— | CH$_3$ | CH$_3$ | 2950, 1716, 1505, 1258, 1204, 1039, 748 |

In general terms, the novel compounds are extremely effective on a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
*Septoria nodorum* in wheat,
*Pyrenophora teres* in barley,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Alternaria solani* in potatoes and tomatoes,
*Plasmopara viticola* in grapes, and
*Fusarium* and *Verticillium* species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, toluene), chlorinated aromatics (e.g., chlorobenzenes), paraffins (e.g., crude oil fractions), alcohols (e.g., methanol, butanol), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt% of active ingredient. The application rates are from 0.05 to 3 kg or more of active ingredient per hectare, depending on the type of effect desired.

The agents and the ready-to-use formulations prepared from then, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 89 is mixed with 10 parts by weight of N-methyl-α-pyrrolidone. A mixture is obtained which is suitable for application in the form of very fine drops.

II. 20 parts by weight of compound no. 100 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 89 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 100 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 89 is well mixed with 3 parts by weight of the sodium salt of diisobutylnaphthalene-α-sulfonic acid, 10 parts by weight of the sodium-salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 100 is intimately mixed with 97 parts by weight of particulate kaolin. A dust is obtained containing 3% by weight of the active ingredient.

VII. 30 parts by weight of compound no. 89 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 100 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 89 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide, N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate, 5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

In the following experiments, the prior art compounds N-tridecyl-2,6-dimethylmorpholine (A) and its acetate (B) were used for comparison purposes.

USE EXAMPLE 1

Action on Wheat Mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. *tritici*). The plants were then set up in the greenhouse at from 20° to 22° C. and a relative humidity of from 75 to 80%. The extent of mildew spread was assessed after 7 days.

The results of this experiment show that active ingredients nos. 89 and 100, when applied as 0.025 and 0.006% (wt%) spray liquors, had a better fungicidal action (90%) than prior art active ingredients A and B (70%).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results obtained in this experiment show that active ingredients nos. 89 and 100, applied as a 0.05% spray liquor, had a good fungicidal action (90%).

We claim:

1. Substituted crotonates of the formula

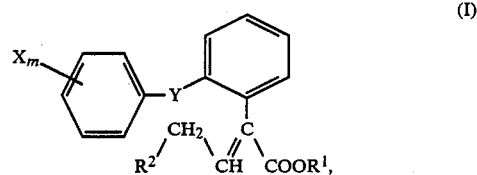

(I)

where $R^1$ is $C_1$–$C_5$-alkyl, $R^2$ is hydrogen, $C_1$–$C_4$-alkyl, X is halogen, cyano, trifluoromethyl, nitro, $C_1$–$C_4$-alkyl, $C_1$–$C_4$-alkoxy, substituted or unsubstituted phenyl, substituted or unsubstituted phenoxy, substituted or unsubstituted benzyloxy or hydrogen, the substituents being identical or different when m is greater than 1, m is from 1 to 5, and Y is methylenoxy, oxymethylene, ethylene, ethenylene, ethynylene or oxygen.

2. Compounds of the formula I as set forth in claim 1, where X is hydrogen, 2-fluoro, 3-fluoro, 4-fluoro, 2-chloro-6-fluoro, 2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert.-butyl, 2,4-dimethyl, 2,6-dimethyl, 2,4,6-trimethyl, 2-methoxy-4-methyl, 4-methoxy-2-methyl, 2-methoxy, 3-methoxy, 4-methoxy, 4-ethoxy, 4-isopropoxy, 2-trifluoromethyl, 3-trifluoromethyl, 4-trifluoromethyl, 2-cyano, 3-cyano, 4-cyano, 3-nitro, 4-nitro, 4-phenyl, 4-benzyloxy, 4-phenoxy, halophenoxy, 4-(2-chloro)-phenoxy, 4-(2,4-dichloro)-phenoxy, $C_1$–$C_4$-alkylphenoxy, 4-(2-methyl)-phenoxy, 3-benzyloxy, halobenzyloxy, 3-(2-chloro)-benzyloxy, 3-(2,4-dichloro)-benzyloxy, 3-(2-fluoro)-benzyloxy, 3-(4-bromo)-benzyloxy, $C_1$–$C_4$-alkylbenzyloxy, 3-(2-methyl)-benzyloxy, 3-phenoxy, 3-(2-chloro)-phenoxy, 3-(2,4-dichloro)-phenoxy, 3-(2-fluoro)phenoxy, 3-(4-bromo)-phenoxy, 3-(2-methyl)-phenoxy, $R^2$ is hydrogen, methyl, ethyl, propyl, butyl, $R^1$ is $C_1$–$C_3$-alkyl, and Y is a —CH$_2$O—, —OCH$_2$—, —CH$_2$—CH$_2$—, CH=CH— or —C≡C— group or is 0.

3. A fungicidal composition containing a compound of the formula I

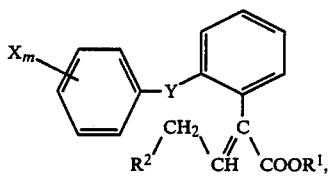

(I)

where R$^1$ is C$_1$–C$_5$-alkyl, R$^2$ is hydrogen, C$_1$–C$_4$-alkyl, X is halogen, cyano, trifluoromethyl, nitro, C$_1$–C$_4$-alkyl, C$_1$–C$_4$-alkoxy, substituted or unsubstituted phenyl, substituted or unsubstituted phenoxy, substituted or unsubstituted benzyloxy or hydrogen, the substituents being identical or different when m is greater than 1, m is from 1 to 5, and Y is methylenoxy, oxymethylene, ethylene, ethenylene, ethynylene or oxygen, and an inert carrier.

4. A process for combating fungi, wherein a compound of the formula I

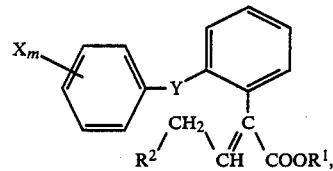

(I)

where R$^1$ is C$_1$–C$_5$-alkyl, R$^2$ is hydrogen, C$_1$–C$_4$-alkyl, X is halogen, cyano, trifluoromethyl, nitro, C$_1$–C$_4$-alkyl, C$_1$–C$_4$-alkoxy, substituted or unsubstituted phenyl, substituted or unsubstituted phenoxy, substituted or unsubstituted benzyloxy or hydrogen, the substituents being identical or different when m is greater than 1, m is from 1 to 5, and Y is methylenoxy, oxymethylene, ethylene, ethenylene, ethynylene or oxygen, is allowed to act on the fungi, or on areas, plants or seed threatened by fungus attack.

5. A compound of the formula I as set forth in claim 1, where R$^1$ is methyl, X is 3-chloro, Y is CH$_2$O and R$^2$ is H.

6. A compound of the formula I as set forth in claim 1, where R$^1$ is methyl, X is 2-methyl, Y is CH$_2$O and R$^2$ is H.

* * * * *